United States Patent
Porter et al.

(10) Patent No.: US 10,265,075 B2
(45) Date of Patent: Apr. 23, 2019

(54) INTRA-ANEURYSM DEVICES

(71) Applicants: Stryker Corporation, Kalamazoo, MI (US); Stryker NV Operations Limited, Dublin (IE)

(72) Inventors: Stephen Christopher Porter, Piedmont, CA (US); Tri D. Tran, Fremont, CA (US); Hanh Ho, San Jose, CA (US); Thach Cao, San Jose, CA (US)

(73) Assignees: STRYKER CORPORATION, Kalamazoo, MI (US); STRYKER EUROPEAN HOLDINGS I, LLC, Kalamazoo, MI (US)

( * ) Notice: Subject to any disclaimer, the term of this patent is extended or adjusted under 35 U.S.C. 154(b) by 974 days.

(21) Appl. No.: 13/887,589

(22) Filed: May 6, 2013

(65) Prior Publication Data
US 2013/0325053 A1    Dec. 5, 2013

Related U.S. Application Data

(63) Continuation of application No. 11/031,421, filed on Jan. 7, 2005, now abandoned.

(51) Int. Cl.
*A61B 17/12* (2006.01)

(52) U.S. Cl.
CPC .. *A61B 17/12113* (2013.01); *A61B 17/12022* (2013.01); *A61B 17/12172* (2013.01); *A61B 2017/12054* (2013.01); *A61B 2017/12063* (2013.01)

(58) Field of Classification Search
CPC ............ A61B 17/12022–17/12195; A61B 2017/00632
USPC ............... 606/191–200; 623/17.11–17.16
See application file for complete search history.

(56) References Cited

U.S. PATENT DOCUMENTS

| | | | |
|---|---|---|---|
| 3,174,851 A | 3/1965 | Buehler | |
| 3,351,463 A | 11/1967 | Rozner | |
| 3,753,700 A | 8/1973 | Harrison et al. | |
| 4,739,768 A | 4/1988 | Engelson | |
| 4,932,975 A * | 6/1990 | Main .................... | A61F 2/44 606/247 |
| 4,994,069 A | 2/1991 | Ritchart et al. | |
| 5,122,136 A | 6/1992 | Guglielmi et al. | |
| 5,284,488 A | 2/1994 | Sideris | |
| 5,342,393 A * | 8/1994 | Stack ................. | A61B 17/0057 24/453 |

(Continued)

FOREIGN PATENT DOCUMENTS

| | | |
|---|---|---|
| WO | 02/45596 | 6/2002 |
| WO | 02/051460 | 7/2002 |

(Continued)

OTHER PUBLICATIONS

Co-owned U.S. Appl. No. 10/745,911.

*Primary Examiner* — Ryan J. Severson
*Assistant Examiner* — Charles M Wei
(74) *Attorney, Agent, or Firm* — Vista IP Law Group LLP

(57) ABSTRACT

Devices for occluding an aneurysm are provided. In particular, the device include an upper member that sits against the dome of the aneurysm, a lower member that sits in the neck of the aneurysm, and a means of adjusting the overall dimensions of the device. Also provided are methods of making and using these devices.

11 Claims, 6 Drawing Sheets

(56) References Cited

U.S. PATENT DOCUMENTS

| | | | |
|---|---|---|---|
| 5,350,399 A | 9/1994 | Eriebacher et al. | |
| 5,354,295 A | 10/1994 | Guglielmi et al. | |
| 5,382,259 A | 1/1995 | Phelps et al. | |
| 5,514,076 A | 5/1996 | Ley | |
| 5,634,936 A | 6/1997 | Linden et al. | |
| 5,690,666 A | 11/1997 | Berenstein et al. | |
| 5,690,667 A | 11/1997 | Gia | |
| 5,733,294 A * | 3/1998 | Forber | A61B 17/12022 606/151 |
| 5,772,669 A | 6/1998 | Vrba | |
| 5,826,587 A | 10/1998 | Berenstein et al. | |
| 5,944,738 A * | 8/1999 | Amplatz | A61B 17/0057 606/213 |
| 6,022,351 A | 2/2000 | Bremer et al. | |
| 6,168,622 B1 * | 1/2001 | Mazzocchi | A61B 17/0057 606/200 |
| 6,280,457 B1 | 1/2001 | Wallace et al. | |
| 6,299,627 B1 | 10/2001 | Eder et al. | |
| 6,375,668 B1 * | 4/2002 | Gifford | A61B 17/12022 606/200 |
| 6,379,368 B1 * | 4/2002 | Corcoran | A61B 17/0057 606/153 |
| 6,391,050 B1 | 5/2002 | Broome | |
| 6,425,914 B1 | 7/2002 | Wallace et al. | |
| 6,458,119 B1 | 10/2002 | Berenstein et al. | |
| 6,533,801 B2 | 3/2003 | Wallace et al. | |
| 6,585,754 B2 | 7/2003 | Wallace et al. | |
| 6,623,493 B2 | 9/2003 | Wallace et al. | |
| 6,669,721 B1 * | 12/2003 | Bose | A61B 17/12022 623/1.15 |
| 6,746,468 B1 | 6/2004 | Sepetka et al. | |
| 2002/0026210 A1 * | 2/2002 | Abdel-Gawwad | A61B 17/12022 606/194 |
| 2003/0097169 A1 * | 5/2003 | Brucker | A61F 2/856 623/1.11 |
| 2003/0195553 A1 * | 10/2003 | Wallace | A61B 17/12022 606/200 |
| 2003/0220666 A1 * | 11/2003 | Mirigian | A61B 17/12022 606/200 |
| 2004/0249462 A1 * | 12/2004 | Huang | A61F 2/441 623/17.13 |
| 2012/0303053 A1 * | 11/2012 | Chen | A61B 17/12113 606/194 |

FOREIGN PATENT DOCUMENTS

| | | |
|---|---|---|
| WO | 03/051444 | 9/2002 |
| WO | 03/086240 | 10/2003 |

* cited by examiner

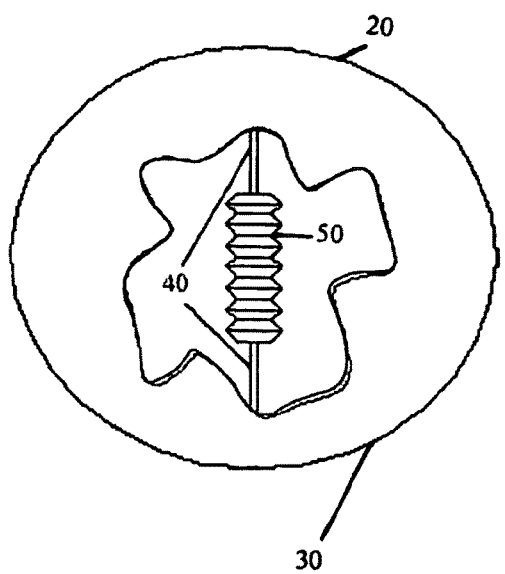
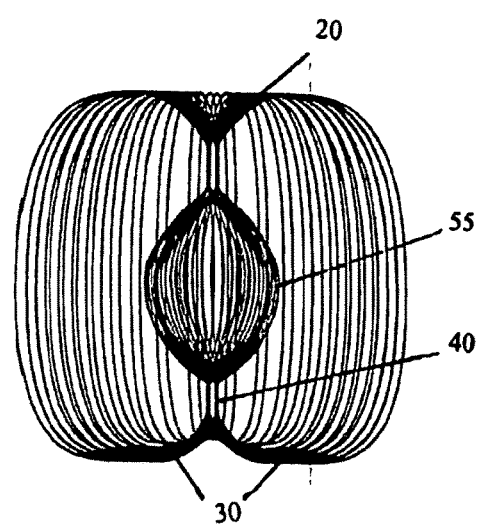
FIG. 5A
FIG. 5B

INTRA-ANEURYSM DEVICES

RELATED APPLICATION DATA

The present application is a continuation of pending U.S. patent application Ser. No. 11/031,421, filed Jan. 7, 2005, the contents of which is incorporated herein by reference in its entirety, as though set forth in full.

FIELD OF THE INVENTION

Compositions and methods for repair and treatment of aneurysms are described. In particular, devices and systems for placement in an aneurysm are disclosed, as are methods of making and using these devices.

BACKGROUND

An aneurysm is a dilation of a blood vessel that poses a risk to health from the potential for rupture, clotting, or dissecting. Rupture of an aneurysm in the brain causes stroke, and rupture of an aneurysm in the abdomen causes shock. Cerebral aneurysms are usually detected in patients as the result of a seizure or hemorrhage and can result in significant morbidity or mortality.

There are a variety of materials and devices which have been used for treatment of aneurysms, including platinum and stainless steel microcoils, polyvinyl alcohol sponges (Ivalone), and other mechanical devices. For example, vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings that may be dimensioned to engage the walls of the vessels. (See, e.g., U.S. Pat. No. 4,994,069 to Ritchart et al.). Other less stiff helically coiled devices have been described, as well as those involving woven braids. See, e.g., U.S. Pat. No. 6,299,627.

U.S. Pat. No. 5,354,295 and its parent, U.S. Pat. No. 5,122,136, both to Guglielmi et al., describe an electrolytically detachable embolic device. Vaso-occlusive coils having little or no inherent secondary shape have also been described. For instance, co-owned U.S. Pat. Nos. 5,690,666; 5,826,587; and 6,458,119 by Berenstein et al., describes coils having little or no shape after introduction into the vascular space. U.S. Pat. No. 5,382,259 describes non-expanding braids covering a primary coil structure.

However, there is a risk that known coil designs will migrate fully or partially out of the aneurysm entrance zone and into the feeding vessel. This risk is particularly high with wide neck aneurysms. Generally, wide neck aneurysms are those in which the neck (the entrance zone) has a diameter that either: (1) is at least 80% of the largest diameter of the aneurysm; or (2) is clinically observed to be too wide effectively to retain vaso-occlusive coils that are deployed using the techniques discussed above. Accordingly, devices for retaining coils within aneurysms have been described. See, e.g., U.S. Pat. No. 6,168,622 and U.S. Patent Application Publication No. 20030195553.

Thus, there remains a need for systems and methods for occluding an aneurysm neck would be desirable, including systems that do not rely on coils that may migrate out of aneurysms.

SUMMARY OF THE INVENTION

Thus, this invention includes novel occlusive devices as well as methods of using and making these devices.

In one aspect, the invention includes a vaso-occlusive device for placement within an aneurysm having a neck and a dome, the device comprising a lower member having a linear configuration prior to deployment and a deployed open configuration, wherein the deployed configuration bridges the neck of the aneurysm; an upper member having a undeployed, linear configuration prior and an open, deployed configuration, wherein the deployed configuration rests against at least a portion of the dome of the aneurysm, and a means of adjusting the overall dimensions of the device. In certain embodiments, the distance between the upper and lower members is adjustable. In other embodiments, the lower and/or upper member is compressible (e.g., deformable against the wall of the aneurysm).

In any of the devices described herein, the upper and lower members may be contiguous or alternatively, the upper and lower members may be separate, for example when the device further comprises an adjustable central member having a proximal end connected to the lower member and distal end connected to the upper member. One or more of the upper member lower member and optional central member may be compressible or may comprise a compressible element. Furthermore, the optional central member may further comprise an extendable member connected to the upper member; and/or an expandable element.

In any of the devices described herein, the upper member may comprise a plurality of axially moveable wires passing through the lumen of the central member, each wire comprising a distal end and a proximal end. In certain embodiments, the distal end of one or more of the wires is attached to the central member and/or to the lower member. The upper member may be compressible or deformable, for example against the dome of an aneurysm, thereby changing the overall dimensions of the device.

In another aspect, the invention includes any of the devices as described herein, which device further comprises one or more detachment junctions, each detachment junction comprising an electrolytically detachable end adapted to detach by imposition of a current thereon. One or more detachment junctions may be positioned between the upper member and a pusher wire and/or between the lower member and a pusher tube.

In another aspect, the invention includes any of the devices as described herein, which device further comprises one or more locking mechanisms. In certain embodiments, the locking mechanism comprises an expandable material, for example a self-expanding element.

In yet another aspect, the invention includes any of the devices as described herein, wherein the upper member comprises a metal, for example, a metal selected from the group consisting of nickel, titanium, platinum, gold, tungsten, iridium and alloys or combinations thereof. In certain embodiments, the upper member comprises the alloy nitinol.

In yet another aspect, the invention includes any of the devices as described herein, wherein the lower member comprises a metal, for example a metal selected from the group consisting of platinum, palladium, rhodium, gold, tungsten and alloys thereof. In certain embodiment, the lower member comprises nitinol.

In yet another aspect, the invention includes any of the devices as described herein, wherein the upper and/or lower member comprises a braid or mesh configuration. In certain embodiments, the lower member comprises a mesh or braid structure. In other embodiments, the lower member comprises a film (e.g., a porous film, a polymer film or a metallic film).

In a still further aspect, the invention includes any of the devices as described herein, which device further comprises an additional component, for example a bioactive component.

In yet another aspect, the invention includes a method of occluding a body cavity comprising introducing a vaso-occlusive device as described herein into the body cavity (e.g., an aneurysm). These and other embodiments of the subject invention will readily occur to those of skill in the art in light of the disclosure herein.

BRIEF DESCRIPTION OF THE FIGURES

In order to better appreciate how the devices, methods and other advantages and objects of the present disclosure, a more particular description will be rendered by reference to specific embodiments thereof, which are illustrated in the accompanying drawings. It is to be understood that the drawings depict only exemplary embodiments and are not to be considered limiting in scope.

FIG. 5, panels A and B, are side views depicting another exemplary embodiment in which the upper and lower members comprise a contiguous element. Panel A depicts contiguous upper and lower members connected by a central member that includes a compressible member. Panel B depicts contiguous upper and lower members that are expandable and an expandable central member.

DESCRIPTION OF THE INVENTION

Occlusive (e.g., embolic) devices are described. The devices described herein find use in vascular and neurovascular indications and are particularly useful in treating aneurysms, for example wide-neck, small-diameter, curved or otherwise difficult to access vasculature, for example aneurysms, such as cerebral aneurysms. Methods of making and using these vaso-occlusive devices also form aspects of this invention.

All publications, patents and patent applications cited herein, whether above or below, are hereby incorporated by reference in their entirety.

It must be noted that, as used in this specification and the appended claims, the singular forms "a", "an", and "the" include plural references unless the content clearly dictates otherwise. Thus, for example, reference to a device comprising "an extendable member" includes devices comprising of two or more elements.

The device is a surgical implement and can be readily deployed, removed and/or repositioned in human vasculature. Typically, the devices include a lower member, an upper member and a means for adjusting the overall dimensions of the device, including, for example, a means of adjusting the distance between the lower and upper members. The upper and lower members may be separate or contiguous elements. In addition, one or both of the upper and lower members may be compressible. The lower member typically sits in the neck of the aneurysm while the upper member sits against the walls (e.g., dome) of the aneurysm.

Overall dimensions of the device are changed using any suitable adjustment means. For example, in certain embodiments, the upper and/or lower member may be moved in relation to each other (e.g., extended, expanded, compressed, etc.) in order to change the overall dimensions of the device. One or more adjustable elements (e.g., a central member) may be employed to facilitate the change the dimensions, for example an extendable central member connecting the lower and upper members may be included.

Depicted in the Figures are exemplary embodiments of the present invention. It will be appreciated that this is for purposes of illustration only and that the various elements depicted can be of other materials or shapes.

Figure 1:
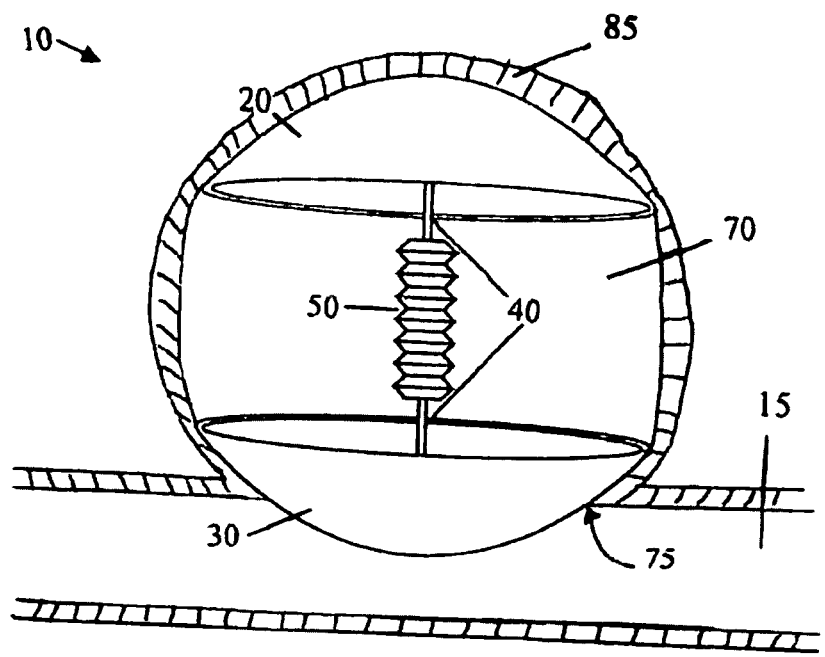
FIG. 1 depicts a side-view of an exemplary assembly as described herein having umbrella shaped upper and lower members. A compressible, spring-like central member connects the upper and lower members and adjusts the distance between the upper and lower members.

Turning to FIG. 1, device (10) constructed in accordance with one embodiment of the present invention is shown in a side-view of a deployed position within an aneurysm (70) of a blood vessel (15). The aneurysm (70) is shown with an oppositely disposed neck (75) and dome (85). As shown in the FIG. 1, upper (20) and lower (30) members have a flared open (umbrella) configuration after deployment that advantageously conforms to the shape of the aneurysm (70). The diameter of the upper member (20) is larger than the neck (75), and thus preferably completely covers the neck (75) upon deployment. Also shown in FIG. 1 is central member (40), which is connected at its distal end to upper member (20) and at its proximal end to lower member (30). Central member (40) also includes a compressible portion (50) that acts as a spring to adjust the distance between and to transfer force from lower member (30) to upper member (20). Central member (40) may also be extendable.

Figure 2:
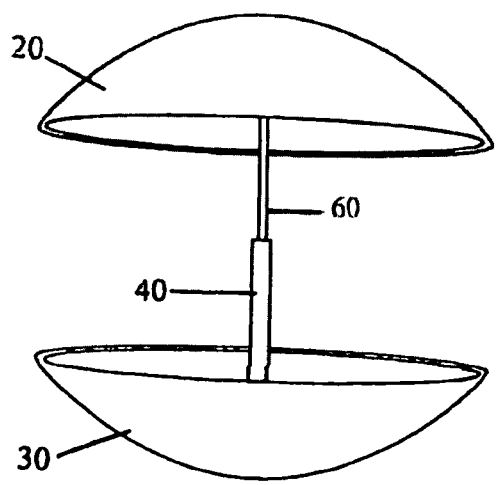
FIG. 2 depicts a side-view of an exemplary assembly as described herein having umbrella shaped upper and lower members. The distance between the upper and lower member can be adjusted by extending or retracting an extendable member located on a central member. The central member connects and extends between the upper and lower members.

FIG. 2 shows a side view of another variation in which the distance between upper (20) and lower (30) members can be adjusted using an extendable member (60) extending from the distal end of central member (40). Extendable member (60) can be extended and retracted from the lumen of the central member (40) to move the upper (20) and lower (30) members closer together or farther apart. In this variation, the upper member (20) is attached to the distal end of the extendable member (60) and the lower member (30) is attached to the distal end of the tubular central member (40). As will be described further herein, movement of the extendable member (60) can be controlled by any suitable actuator.

Figure 3:
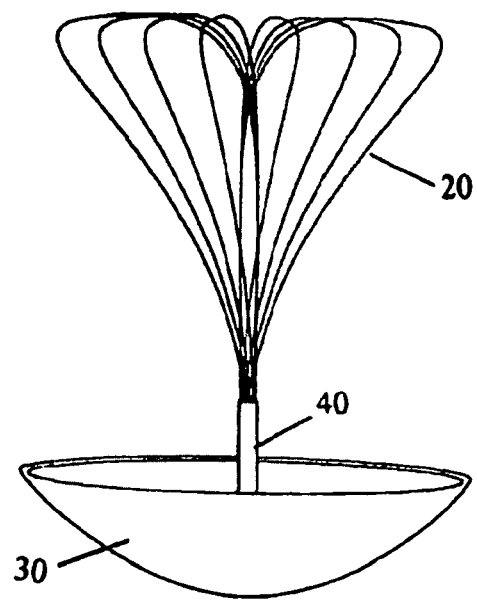
FIG. 3 depicts a side view of another exemplary assembly as described herein having an umbrella shaped lower member from which a central tubular member extends. The central member may be integral to or separate from the lower member. Upper member comprises a plurality of individual members that extend from and loop back into the central member. Upper member elements are extendable and retractable through the central member.

FIG. 3 shows a side view of another variation in which the overall dimensions are adjusted using an extendable upper member (20). Upper member (20) comprises a plurality of moveable elements (e.g., wires or microcoils) that extend from an optional central member (40). In this variation, the plurality of extendable members that comprise upper member (20) form loops as they extend from and back into a lumen in the central member (40). The distal ends of the wires are shown attached to the central member (40) while the proximal ends can be extended or retracted by an operator until the device has the desired overall dimensions (e.g., the loop portion abuts the dome of the aneurysm). In certain embodiments, the wires making up the loops of the upper member may be compressed against the upper wall of the aneurysm upon deployment and thereby change the distance between the uppermost portion of the device and the lower member.

Figure 4:
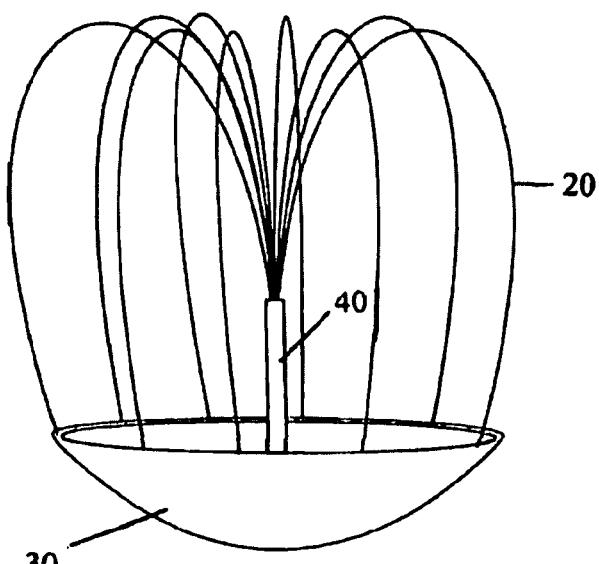
FIG. 4 depicts a side view of another exemplary assembly as described herein having an umbrella shaped lower member from which a central tubular member extends. The central member may be integral to or separate from the lower member. Upper member comprises a plurality of individual members that extend from and the central member. Upper member elements are attached at their distal ends to the lower member and may be extended or retracted through the central member to change the overall dimensions of the device.

FIG. 4 depicts a side view of a variation similar to that shown in FIG. 3 in which the distal ends of the plurality of moveable upper member elements (20) are attached to the lower member (30) rather than the central member (40). As with the embodiment shown in FIG. 3, the proximal ends can be extended or refracted by an operator, thereby forcing the loop portion against the dome of the aneurysm. Also as shown in FIG. 3, the wires may be compressed against the upper wall of the aneurysm upon deployment, thereby changing the overall configuration of the device.

FIG. 5, panels A and B, depict another variation in which the upper member (20) and lower member (30) are a single structure. Panel A is a side view of an exemplary embodiment in which upper (20) and lower (30) members are connected by central member (40). Central member further comprises a compressible portion (50) to adjust distance between upper and lower members. Panel B is a side view of an exemplary embodiment in which upper (20) and lower (30) members comprise a plurality of wires that can expand the overall diameter of the device. Central member (40) also comprises an expandable member (55).

In embodiments in which the upper and lower members are contiguous, the contiguous structure may take any number of forms, including but not limited to, wires (FIG. 5B), braided or woven configurations, solid configurations (FIG. 5A) and the like. It will be apparent that, as a whole, the materials making up contiguous upper and lower member structures may vary in different portions of the structure. For example, in braided or woven structures, the tightness of the braid or weave may be different in the upper portion as compared to the lower portion. Similarly, different additional components may be used in different portions of a contiguous upper and lower member structure.

As shown in the Figures, the overall dimensions of the devices described herein are adjustable, thereby facilitating a transfer of force between the lower member (in the neck) to the upper member (the dome of the aneurysm). The dimensions can be adjusted (and force transferred) in a variety of ways, including but not limited to, the inclusion a moveable central member; a moveable upper member; springs; and/or expandable elements such as balloons. Whatever force transfers design or combinations of designs are employed, the adjustable nature of the dimension(s) of the devices described herein aid in ensuring that the lower member sits in the neck the aneurysm while the upper member presses safely against the dome of the aneurysm. Preferably, the area of contact between the upper and the aneurysm wall is maximized so as to distribute the force across the widest possible area and thus exert the least amount of pressure on the aneurysm wall. Furthermore, it is to be understood that one or more design features shown in the Figures and described herein can be combined into one device.

Although the devices described herein are capable of retaining finer vaso-occlusive devices (e.g., coils, liquid embolics, etc.) within the aneurysm, they are also capable of functioning as vaso-occlusive devices by themselves. As can be appreciated by one of ordinary skill in the art, the force-transfer effect achieved by including one or more adjustment means (e.g., moveable elements) serves to anchor the device in the aneurysm and reinforce the lower member so that it is able to remain stably situated across the aneurysm neck while diverting the flow of blood from within the aneurysm.

As will be apparent, the devices described herein may conform to a range of shapes and sizes of aneurysms since the dimensions are adjustable. Furthermore, following the teachings described herein, the devices can be sized to fit aneurysms ranging in size from millimeters in diameter to centimeters in diameter. In this way, the operator can select a device of a generally suitable size for the particular indication and adjust it to fit securely by conforming the upper member to the dome of the aneurysm.

As noted above, the lower member and upper members may assume a variety of structures, for example, umbrella, dome, balloon, teardrop or cone shape. The deployed configuration of the lower member is preferably such that it sits in and covers the neck of the aneurysm. Similarly, the deployed configuration of the upper member is such that it sits safely against the dome of the aneurysm (e.g., back inner wall). Generally, the overall structure of the upper member is typically more variable than that of the lower member and includes, but is not limited to, configuration such as umbrella shapes, strings or wires formed into loops, etc. One or both of the lower and upper members may also include thin-film, braided, mesh like or basket type structures. Furthermore, the upper and lower members may be a single element, for example expandable structures, for example as shown in FIG. 5.

Upper and lower members can be constructed from a wide variety of materials, including, but not limited to, metals, metal alloys, polymers or combinations thereof. See, e.g., U.S. Pat. Nos. 6,585,754 and 6,280,457 for a description of various polymers. Non-limiting examples of suitable metals include, Platinum Group metals, especially platinum, rhodium, palladium, rhenium, as well as tungsten, gold, silver, tantalum, stainless steel and alloys of these metals. Preferably, the lower member comprises a material that maintains its shape despite being subjected to high stress, for example, "super-elastic alloys" such as nickel/titanium alloys (48-58 atomic % nickel and optionally containing modest amounts of iron); copper/zinc alloys (38-42 weight % zinc); copper/zinc alloys containing 1-10 weight % of beryllium, silicon, tin, aluminum, or gallium; or nickel/aluminum alloys (36-38 atomic % aluminum). Particularly preferred are the alloys described in U.S. Pat. Nos. 3,174,851; 3,351,463; and 3,753,700. Especially preferred is the titanium/nickel alloy known as "nitinol."

Shape memory alloys comprise a unique class of metal alloys that, once trained, are configured to "remember" a pre-selected shape, i.e., deployed shape, and can return to the pre-selected shape even if subsequently reshaped. To be trained to "remember" a first pre-selected shape, the shape memory alloy is molded and heated at or above a training, or austenite, temperature to place the shape memory alloy in an austenite phase. In the austenite phase, the shape memory alloy is formed in the first pre-selected shape and then, once formed, is permitted to cool to a martensite finish temperature, whereupon the shape memory alloy enters a martensite phase. The martensite finish temperature can be any temperature that is less than the training temperature. Upon entering the martensite phase, the shape memory alloy has been trained to "remember" the first pre-selected shape. While in the martensite phase, the alloy is in a soft state and is formed into a second pre-selected shape, e.g., an undeployed shape. The shape memory alloy in the martensite phase is configured to maintain the second pre-selected shape and, if subsequently reheated to an activation temperature, automatically returns to the first pre-selected shape. The activation temperature can comprise any temperature that is greater than the martensite finish temperature and generally approximately equals the training temperature. Once the first pre-selected shape has been recovered, the shape memory alloy is configured to maintain the first pre-selected shape irrespective of temperature. Generally, as can be appreciated by one of ordinary skill in the art, the training, martensite finishing, and activation temperatures for a shape memory alloy are adjustable, depending on the composition. For example, a slight extra amount of Nickel added to a NiTi alloy composition can change the training temperature from approximately 0° C. to 100° C. The lower member may also comprise a shape memory polymer such as those described in International Publication WO 03/51444.

In certain embodiments, the upper and/or lower members of the devices described herein may also be moveable. For instance, as shown in FIG. 3 and FIG. 4, the upper member may comprise a plurality of elements that can be extended or retracted (typically through the central member) to change the overall dimensions of the device and ensure that the upper member sits against the dome of the aneurysm and the lower member sits in the neck.

As noted above, the upper and lower members may be attached directly to each other at one or more locations as shown in FIG. 4 or may be attached via the central member or other additional element as shown in FIGS. 1-3. Alternatively, the upper and lower members may be contiguous, forming a single member as shown in FIG. 5.

When present, the central member may be made of a wide variety of materials and may assume many shapes. The central member may be a tubular or coiled structure, including a lumen therethrough, or may be a wire (e.g., a wire or other structure that serves as both central member and guide/pusher wire). The central member may comprise expandable elements, for example as shown in FIG. 5B.

In certain embodiments, the central member (or an element attached thereto or extending therefrom) is moveable. For instance, as shown in FIG. 2, the central member can have an axially moveable extendable member passing through and extending from the lumen of the central member. The upper member is attached to the extendable member and by extending or retracting the extendable member, the overall dimension of the device can be changed and bolster the upper member. As noted above, various adjustment means may be used in conjunction with the central member to change the dimensions of the device and thereby transfer force between the upper and lower members including, but not limited to, compressible elements (e.g., elements having characteristics of a spring as depicted in FIG. 1 and FIG. 5A) and/or an expandable element such as a braid, woven structure or balloon-like structure (FIG. 5B).

It will be apparent that the devices described herein can be made in a wide range of sizes in order to fit any size aneurysm. As described above, the operator (surgeon) will typically image the aneurysm and determine the approximate dimensions, for example from dome to neck. The appropriate size device can then be selected and positioned within the aneurysm as described herein.

Figure 6A:
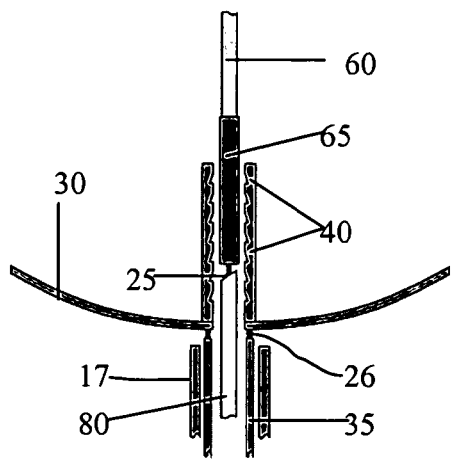
FIG. 6, panels A and B, are side views of an exemplary locking mechanism. Panel A depicts the device in an unlocked position in which the distance between upper and lower members can be adjusted. Panel B depicts the locked position in which the distance between the upper and lower members remains fixed. Also shown is detachment junction for releasing the device once the desired configuration is achieved.
Figure 6B:
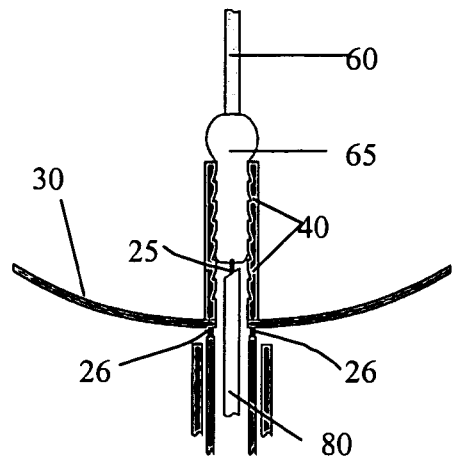
Figure 7A:
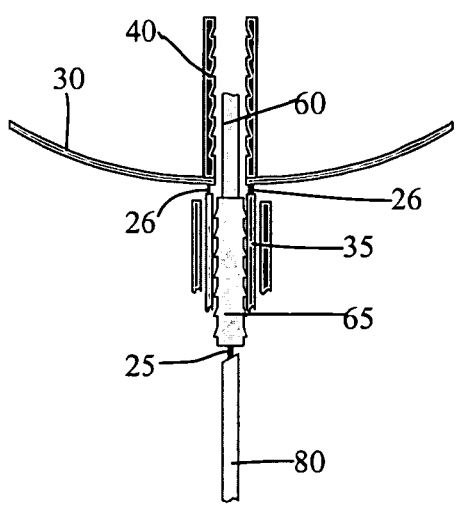
FIG. 7, panels A and B, are side views of an exemplary locking mechanism. Panel A depicts the device in an unlocked position in which the distance between upper and lower members can be adjusted. Panel B depicts the locked position in which the distance between the upper and lower members remains fixed. Also shown is detachment junction for releasing the device once the desired configuration is achieved.
Figure 7B:
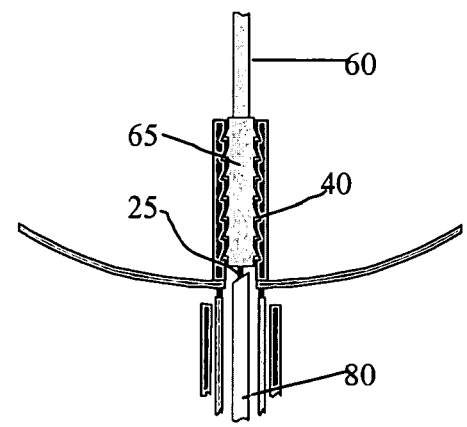
Figure 8A:
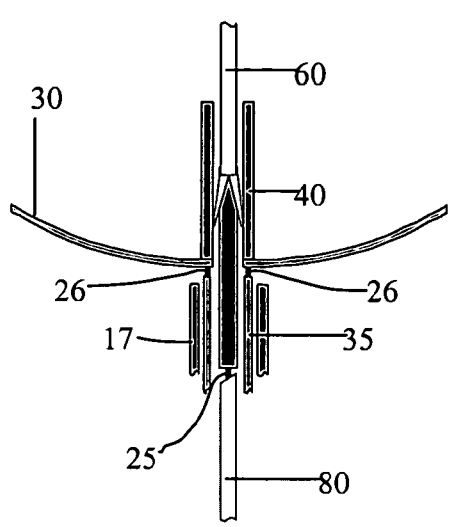
FIG. 8, panels A and B, are side views of an exemplary locking mechanism. Panel A depicts the device in an unlocked position in which the distance between upper and lower members can be adjusted. Panel B depicts the locked position in which the distance between the upper and lower members remains fixed. Also shown is detachment junction for releasing the device once the desired configuration is achieved.
Figure 8B:
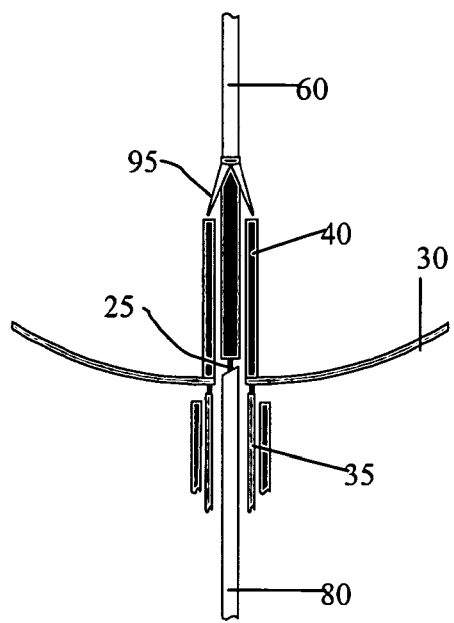
Figure 9A:
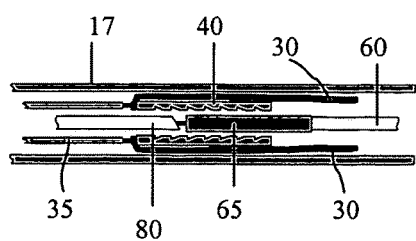
FIG. 9, panels A to D, depict exemplary deployment procedure. Panel A depicts the lower portion of the device as it is advanced through the delivery catheter by the pusher wire. Panel B shows expansion of the lower member after extrusion from a constraining member (e.g., pusher catheter and/or sheath). Panel C shows the device after it is locked in place via an expandable material and after the pusher wire has been detached. Panel D shows detachment of the pusher catheter and removal of the pusher and delivery catheters. Although all panels show partial side-views depicting lower and central members, it will be appreciated that the devices shown will also include upper members as described herein.
Figure 9B:
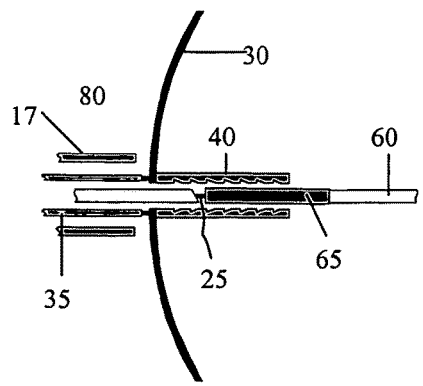
Figure 9C:
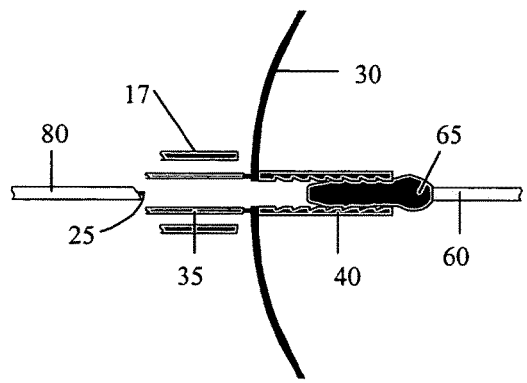
Figure 9D:
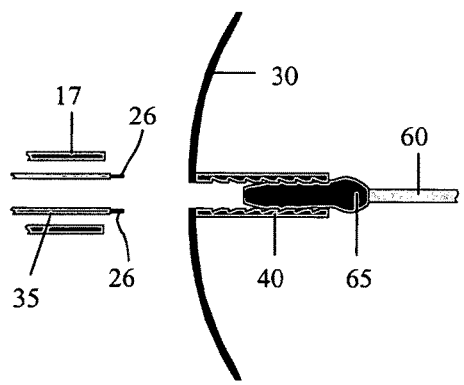

In certain embodiments, the device is secured in the desired dimensions by employing one or more locking mechanisms are generally included. A variety of locking mechanisms can be used, as shown in FIGS. 6, 7 and 8. For convenience, exemplary locking mechanisms are depicted as positioned on extendable members (60), which is shown passing through the lumen of central element (40). However, it will be apparent that the extendable member (60) shown in the Figures could also be the upper member (20). Also shown in FIGS. 6, 7 and 8 are lower member (30), pusher (80), detachment junctions (25, 26), delivery catheter (or sheath) (17), and stabilizer catheter (or "pusher tube") (35). Delivery catheter (17) and pusher tube (35) are coaxial.

In the variation shown in FIG. 6, an expandable material is used to lock the device in the desired dimensions (e.g., maintain the upper and lower members at the desired distance from each other). FIG. 6, panel A, depicts lower member (30) and extendable member (60) passing through central member (40). At the proximal end of extendable member (60) is detachment junction (25). Extendable member (60) further comprises expandable material (65) that may be expanded upon exposure to one or more selected stimuli. Non-limiting examples of suitable stimuli include exposure to liquid, air (e.g., balloon), change in temperature, electromagnetic radiation and the like. Panel B shows expandable material (65) in its expanded configuration, which locks the device in the desired overall configuration, both by fitting the expandable material (65) into the grooves of the lumen of central member (40) and by providing a stop (90) that is larger than the lumen of the central member (40) and does not allow the extendable member (60) to be moved.

FIG. 7 shows an embodiment in which the device is locked into place by interlocking grooves. In particular, extendable member (60) includes grooves (65) that interlock with the lumen of central member (40). As long as the extendable member is attached to the pusher (80), the extendable member (60) can be moved through the lumen of the central member (40). Once the desired configuration (distance between upper and lower members) is achieved (FIG. 6B), the extendable member (60) is detached from the pusher (80) at the detachment junction (25). Once detached, the overall dimensions of the device remain constant due to the interlocking mechanism.

FIG. 8 shows another exemplary locking mechanism that includes an expanding flange-like mechanism (95). Panel A, shows the device as the operator pushes the extendable member (60) through the central member (40) in order to place the upper member against the dome of the aneurysm. Panel B shows the device as locked into place with the expandable flange (95) in its expanded position.

Also as shown in FIGS. 6-9, the device may also include one or more detachment junctions (25, 26), for example so that the upper member can be extended to the proper size for the aneurysm and the portion(s) of the upper member that are not needed detached from the pusher wire and removed from the vessel. In certain embodiments, the lower member may be detachably joined to a pusher tube (35). The pusher tube is preferably detached (via detachment junctions (26)) and removed after deployment. Any of the devices described herein may further comprise one or more additional detachment junctions, which is(are) severable by the same or different mechanisms. The detachment junction may be connected to a pusher element, such as a pusher wire or a tubular structure such as a stabilizer catheter ("pusher tube").

The detachment junction can be positioned anywhere on the device, for example at one or both ends of the device. In certain embodiments, the detachment junction(s) is(are) positioned where the extendable member or upper member is attached to an actuator or locking member. In other embodiments, the detachment junction(s) is(are) positioned at the junction between a pusher tube and the lower member or the central member. In still other embodiments, for example as shown in FIG. 9, panels A-D, detachment junction (25) is positioned the junction of the device and actuator while additional detachment junctions (26) are positioned at the junctions of the pusher tube (35) and upper member (30).

In certain embodiments, the severable junction(s) are, an electrolytically detachable assembly adapted to detach by imposition of a current; a mechanically detachable assembly adapted to detach by movement or pressure; a thermally detachable assembly adapted to detach by localized delivery of heat to the junction; a radiation detachable assembly adapted to detach by delivery of electromagnetic radiation to the junction or combinations thereof.

Furthermore, one or more actuators may be included so that an operator can manipulate the shape or position of the device. For example, the moveable members may be attached, either directly or through another element such as a pusher wire, to an actuator. In certain embodiments, the pusher wire both advances the device into the aneurysm and acts as the actuator to adjust the overall dimensions. As noted above, a pusher wire can serve as guide wire and, optionally actuator. For example, the extendable element (60) of FIG. 2 can be the pusher wire that is attached to the upper member (20) and extendable through the central member (40). Similarly, the pusher wire can be attached to the central member to actuate expansion of one or more components. (FIG. 5B). FIGS. 6-9 show pusher wire (80) that also actuates movement of the device. Additionally, actuators may include one or more handles, dials or the like with which the operator (e.g., surgeon placing the device) controls movement of the device, adjusts the dimensions (e.g., by changing the distance between the upper and lower members and/or expanding a balloon or basket shaped structure) once in the aneurysm and/or locks the device into a desired configuration.

The devices described herein may also comprise additional components, such as co-solvents, plasticizers, coalescing solvents, bioactive agents, antimicrobial agents, antithrombogenic agents, antibiotics, pigments, radiopacifiers and/or ion conductors which may be coated using any suitable method or may be incorporated into the element(s) during production. See, e.g., co-owned U.S. patent application Ser. No. 10/745,911, U.S. Pat. No. 6,585,754 and WO 02/051460, incorporated by reference in their entireties herein.

As noted elsewhere, the location of the device is preferably visible using fluoroscopy. A highly preferred method is to ensure that at least some of the elements making up the device are provided with significant radio-visibility via the placement of a radio-opaque covering on these elements. A metallic coating of a metal having comparatively more visibility, during fluoroscopic use, than stainless steel is preferred. Such metals are well known but include gold and members of the Platinum Group described above.

As noted above, one of more of the elements may also be secured to each other at one or more locations. For example, to the extent that various elements are thermoplastic, they may be melted or fused to other elements of the devices. Alternatively, they may be glued or otherwise fastened. Furthermore, the various elements may be secured to each other in one or more locations.

Methods of Use

The devices described herein are often introduced into a selected site using the procedure outlined below. This procedure may be used in treating a variety of maladies. For instance in the treatment of an aneurysm, the aneurysm itself will be filled (partially or fully) with the devices described herein.

Generally, devices as described above are delivered to an aneurysm via a delivery catheter. It will be apparent that the device is preferably delivered in an undeployed shape, e.g., a tubular shape and that, following deployment, the device assumes a different three-dimensional configuration. The device may be self-configuring (e.g., self-expanding) upon deployment, may require actuation by one or more stimuli and/or may be partially self-configuring and partially shaped by application of one or more stimuli.

Self-configuring materials include shape memory alloys and polymers, described above. Thus, the super-elastic characteristics of these materials allow the device to be deployed in a compressed configuration and upon deployment, to assume its three-dimensional configuration. It is to be understood that the three-dimensional configuration assumed by self-configuring devices may also be shaped further (e.g., changing the distance between lower and upper members) using one or more stimuli described below.

In other embodiments, the device assumes a deployed configuration upon the application of one or more appropriate stimuli. For example, the device may be configured so as to achieve its deployed shape when exposed to body temperature (e.g., temperature of the aneurysm). This can be readily achieved by adjusting the training and activation temperatures to be at, or just below, the temperature of the aneurysm (e.g., approximately 37° C.). The martensite temperature is adjusted to be at a lower temperature. With these temperatures set, the device is heated to, or above the training temperature (austenite phase) and shaped into its desired deployed shape, as described above. Then, the temperature is lowered to, or below, the martensite finish temperature and shaped into its desired undeployed shape. Subsequently, the device is then placed inside the catheter for delivery. The catheter can be constructed of a material that insulates the device from the outside environment and maintains the temperature of the device below the activation temperature. Thus, when the catheter is inserted into the lumen of the blood vessel, the device does not expand into its deployed shape within the catheter.

Other stimuli that can be used to change the configuration of the device upon deployment include application of electromagnetic radiation (light), electricity, mechanical pressure, etc. In certain embodiments, the device self-expands and, subsequently, one or more stimuli are also applied to achieve the desired configuration and/or to lock the device in the desired configuration.

Conventional catheter insertion and navigational techniques involving guidewires or flow-directed devices may be used to access the site with a catheter. The mechanism will be such as to be capable of being advanced entirely through the catheter to place vaso-occlusive device at the target site but yet with a sufficient portion of the distal end of the delivery mechanism protruding from the distal end of the catheter to enable detachment of the implantable vaso-occlusive device. In certain embodiments, the device (e.g., lower member) is attached to the distal end of a retractable sheath (also referred to as a pusher tube). The device may be extended and retracted from the pusher tube (by the actuator) and delivery catheter until the desired configuration is achieved, at which point, the pusher tube is detached from the device and withdrawn along with the delivery catheter. FIG. 9.

For use in peripheral or neural surgeries, the delivery mechanism will normally be about 100-200 cm in length, more normally 130-180 cm in length. The diameter of the delivery mechanism is usually in the range of 0.25 to about 2.0 mm. Briefly, occlusive devices (and/or additional components) described herein are typically loaded into a carrier for introduction into a delivery catheter and introduced to the chosen site using the procedure outlined below. This procedure may be used in treating a variety of maladies. For instance, in treatment of an aneurysm, the aneurysm itself may be filled with a device as described herein which cause formation of an emboli and, at some later time, is at least partially replaced by neovascularized collagenous material formed around the implanted vaso-occlusive devices.

A selected site is reached through the vascular system using a collection of specifically chosen catheters and/or guide wires. It is clear that should the site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter. Once the distal end of the catheter is positioned at the site, often by locating its distal end through the use of radiopaque marker material and fluoroscopy, the catheter is cleared. For instance, if a guidewire has been used to position the catheter, it is withdrawn from the catheter and then the assembly, for example including the vaso-occlusive device at the distal end, is advanced through the catheter.

In certain embodiments, the delivery catheter comprises a retractable sheath (or pusher tube) at its distal end that surrounds the device to be delivered. Typically, the retractable distal sheath includes a pull back means operatively connected to the distal sheath. The catheter may be constructed and arranged such that distal end of the sheath does not extend past the distal end catheter. Alternatively, the distal end of the sheath may extend beyond the distal end of the delivery catheter, for example so that is extrudes the device directly into the target site. In certain preferred embodiments, the devices described herein are detachably linked to the distal end of a retractable sheath. FIGS. 6-9. Non-limiting examples of suitable delivery catheters will be known to those of skill in the art in view of the teachings herein. See, also, U.S. Pat. Nos. 6,425,914; 5,772,669; and 6,391,050.

Once the selected site has been reached, the vaso-occlusive device is extruded, for example by retracting the sheath surrounding and mounted to the device. Preferably, the vaso-occlusive device is loaded onto the pusher wire and/or tube via a mechanically or electrolytically cleavable junction (e.g., a GDC-type junction that can be severed by application of heat, electrolysis, electrodynamic activation or other means). Additionally, the vaso-occlusive device can be designed to include multiple detachment points, as described in co-owned U.S. Pat. Nos. 6,623,493 and 6,533,801 and International Patent publication WO 02/45596. Once detached the devices are held in place by gravity, shape, size, volume, magnetic field or combinations thereof.

After deployment and prior to detachment from the pusher wire and/or pusher tube, it may be preferable to lock the device in the desired configuration. This can be accomplished in any number of ways, for example, using locking elements as shown in FIGS. 6-8. As can be seen in the exemplary embodiments depicted in these Figures, the inclusion of one or more locking mechanisms helps ensure the overall configuration of the device and, accordingly, the efficient transfer of force between the upper and lower members and the surfaces of the aneurysm they contact. Detachment from the pusher wire and/or pusher tube can then be accomplished as described above.

An exemplary deployment scheme is shown in FIG. 9. FIG. 9A shows a side-view of the lower and central members of an exemplary device as described herein as it is advanced through the delivery catheter (17) by the pusher wire (80). Lower member (30) is constrained in linear position by delivery catheter (17) and by pusher catheter sheath (35). Extendable member (60) further comprises an expandable member (65). Central member (40) is depicted with inward-facing grooves. FIG. 9B depicts how lower member (30) assumes an expanded, three-dimensional configuration upon extrusion from pusher catheter sheath (35) and delivery catheter (17). FIG. 9C depicts the device in a locked position after expansion of expandable member (65). In addition, pusher wire is shown as detached from extendable member (60) via detachment junction (25). FIG. 9D shows the withdrawal of the delivery catheter (17) and pusher catheter (35), leaving the device in place where desired. Pusher catheter (35) is detached from lower member (30) via detachment junctions (26).

Modifications of the procedure and vaso-occlusive devices described above, and the methods of using them in keeping with this invention will be apparent to those having skill in this mechanical and surgical art. These variations are intended to be within the scope of the claims that follow.

What is claimed is:

1. A vaso-occlusive device configured for placement within an aneurysm, the aneurysm having a neck and a sac, the device comprising:
    a self-expanding resilient body having a linear configuration for deployment through a delivery catheter, and an expanded, substantially spherical deployed configuration, wherein in the deployed configuration, the resilient body bridges the neck of the aneurysm and occludes the aneurysm sac when the device is placed within the aneurysm,
    wherein the resilient body comprises a plurality of wires that define a substantially spherical interior region when the resilient body is in the deployed configuration,
    each wire having a proximal end and a distal end, wherein the proximal ends of the wires are coupled together in a configuration forming an external concavity at a proximal end of the resilient body, and the distal ends of the wires are coupled together in a configuration forming an external concavity at a distal end of the resilient body, respectively, when the resilient body is in the deployed configuration.

2. The vaso-occlusive device of claim 1, further comprising a central member having a proximal end that is coupled to the proximal end of the resilient body, and a distal end that is coupled to the distal end of the resilient body.

3. The vaso-occlusive device of claim 2, wherein the proximal ends of the wires are coupled to the central member.

4. The vaso-occlusive device of claim 2, wherein the distal ends of the wires are coupled to the central member.

5. The vaso-occlusive of claim 1, further comprising a mechanical or electrolytic detachment junction.

6. The vaso-occlusive device of claim 5, wherein the detachment junction is disposed between the resilient body and a pusher wire slidably disposed within a delivery catheter.

7. The vaso-occlusive device of claim 1, wherein the device is made from a biocompatible material.

8. The vaso-occlusive device of claim 1, further comprising a bioactive agent.

9. A vaso-occlusive assembly, comprising:
    a delivery catheter;
    an elongated pusher member at least partially slidably disposed within the delivery catheter;
    an implantable vaso-occlusive device coupled to a distal end of the elongated pusher member within the delivery catheter, the vaso-occlusive device configured for implantation in an aneurysm sac and having a collapsed delivery configuration when restrained within the delivery catheter, and an expanded deployed configuration after being released from the delivery catheter into the aneurysm sac, the vaso-occlusive device comprising
        a detachment junction detachably coupled to a distal end of the elongated pusher member; and
        a self-expanding resilient body having a substantially spherical deployed configuration, wherein in the deployed configuration, the resilient body bridges the neck of the aneurysm and occludes the aneurysm sac when the device is placed within the aneurysm,
    wherein the resilient body comprises a plurality of wires that define a substantially spherical interior region when the resilient body is in the deployed configuration,
    each wire having a proximal end and a distal end, wherein the proximal ends of the wires are coupled together in a configuration forming an external concavity at a proximal end of the resilient body, and the distal ends of the wires are coupled together in a configuration forming an external concavity at a distal end of the resilient body, respectively, when the resilient body is in the deployed configuration.

10. The vaso-occlusive assembly of claim 9, wherein dimensions of the deployed configuration of the vaso-occlusive device are adjustable.

11. The vaso-occlusive assembly of claim 9, wherein the detachment junction comprises a mechanical or electrolytic detachment junction.

* * * * *

(12) EX PARTE REEXAMINATION CERTIFICATE (12469th)
United States Patent
Porter et al.

(10) Number: US 10,265,075 C1
(45) Certificate Issued: Dec. 18, 2023

(54) INTRA-ANEURYSM DEVICES

(71) Applicants: Stryker Corporation, Kalamazoo, MI (US); Stryker NV Operations Limited, Dublin (IE)

(72) Inventors: Stephen Christopher Porter, Piedmont, CA (US); Tri D. Tran, Fremont, CA (US); Hanh Ho, San Jose, CA (US); Thach Cao, San Jose, CA (US)

(73) Assignee: Stryker European Operations Holdings LLC

Reexamination Request:
No. 90/019,018, Aug. 19, 2021

Reexamination Certificate for:
Patent No.: 10,265,075
Issued: Apr. 23, 2019
Appl. No.: 13/887,589
Filed: May 6, 2013

Related U.S. Application Data

(63) Continuation of application No. 11/031,421, filed on Jan. 7, 2005, now abandoned.

(51) Int. Cl.
*A61B 17/12* (2006.01)

(52) U.S. Cl.
CPC .. *A61B 17/12113* (2013.01); *A61B 17/12022* (2013.01); *A61B 17/12172* (2013.01); *A61B 2017/12054* (2013.01); *A61B 2017/12063* (2013.01)

(58) Field of Classification Search
None
See application file for complete search history.

(56) References Cited

To view the complete listing of prior art documents cited during the proceeding for Reexamination Control Number 90/019,018, please refer to the USPTO's Patent Electronic System.

*Primary Examiner* — Catherine S Williams

(57) ABSTRACT

Devices for occluding an aneurysm are provided. In particular, the device include an upper member that sits against the dome of the aneurysm, a lower member that sits in the neck of the aneurysm, and a means of adjusting the overall dimensions of the device. Also provided are methods of making and using these devices.

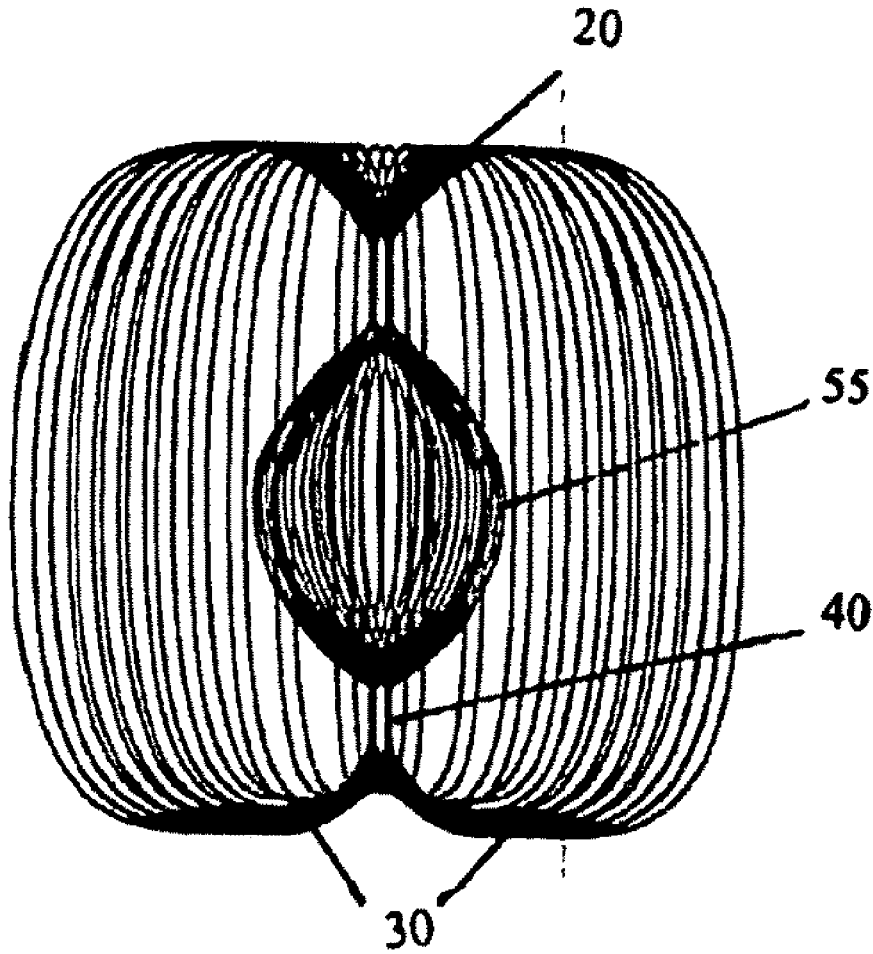

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1 and 5-11 are cancelled.

Claims 2-4 were not reexamined.

\* \* \* \* \*